(12) United States Patent
Yamaji et al.

(10) Patent No.: US 10,156,460 B2
(45) Date of Patent: Dec. 18, 2018

(54) SENSOR MOUNTING BRACKET

(71) Applicant: FUJITSU LIMITED, Kawasaki-shi, Kanagawa (JP)

(72) Inventors: Takayuki Yamaji, Yokohama (JP); Seiki Ishii, Kawasaki (JP); Hiroyuki Fujita, Suginami (JP)

(73) Assignee: FUJITSU LIMITED, Kawasaki-Shi (JP)

( * ) Notice: Subject to any disclaimer, the term of this patent is extended or adjusted under 35 U.S.C. 154(b) by 59 days.

(21) Appl. No.: 15/283,549

(22) Filed: Oct. 3, 2016

(65) Prior Publication Data

US 2017/0138770 A1 May 18, 2017

(30) Foreign Application Priority Data

Nov. 18, 2015 (JP) .................................. 2015-225973

(51) Int. Cl.
| | | |
|---|---|---|
| *F16M 13/00* | (2006.01) | |
| *G01D 11/30* | (2006.01) | |
| *G01S 13/88* | (2006.01) | |
| *A61B 5/024* | (2006.01) | |
| *A61B 5/05* | (2006.01) | |

(Continued)

(52) U.S. Cl.
CPC .............. *G01D 11/30* (2013.01); *A61B 5/024* (2013.01); *A61B 5/0507* (2013.01); *A61B 5/113* (2013.01);
(Continued)

(58) Field of Classification Search
CPC ... G01D 11/30; G01S 13/88; G01S 2015/937; G01S 2015/938; A61B 5/024;
(Continued)

(56) References Cited

U.S. PATENT DOCUMENTS 1,116,240 A 11/1914 Canfield
1,742,489 A * 1/1930 Sundgren ............... B21D 7/063
72/457

(Continued)

FOREIGN PATENT DOCUMENTS

| CN | 204340686 | * | 5/2015 |
|---|---|---|---|
| CN | 104709220 A | | 6/2015 |
| JP | 2-74715 | | 6/1990 |

OTHER PUBLICATIONS

Espacenet Bibliographic data, Chinese Publication No. 10470922 A, published Jun. 17, 2015.*

(Continued)

*Primary Examiner* — Robert R Raevis
(74) *Attorney, Agent, or Firm* — Staas & Halsey LLP

(57) ABSTRACT

A sensor mounting bracket includes: a first plate portion, a second plate portion, and a coupling element coupling the first and second plate portions. When X, Y, and Z axes perpendicular to each other are assumed, a second normal vector normal to a second mounting surface of the second plate portion has Y and Z components greater than 0 in a first state in which the first reference part is aligned with X direction and a first mounting surface of the first plate portion is in XZ plane, and a first normal vector normal to the first mounting surface has Y and Z components greater than 0 in a second state in which the second reference part is aligned with X direction and the second mounting surface is in XZ plane, the first normal vector being oriented differently from the second normal vector.

12 Claims, 17 Drawing Sheets

(51) Int. Cl.
  *A61B 5/11*   (2006.01)
  *A61B 5/113*  (2006.01)
  *F16M 11/22*  (2006.01)
  *F16M 13/02*  (2006.01)
  *G01K 7/00*   (2006.01)
  *H04R 1/02*   (2006.01)

(52) U.S. Cl.
  CPC ............ *A61B 5/1118* (2013.01); *F16M 11/22* (2013.01); *F16M 13/02* (2013.01); *G01K 7/00* (2013.01); *G01S 13/88* (2013.01); *H04R 1/026* (2013.01); *A61B 2562/00* (2013.01)

(58) Field of Classification Search
  CPC ... A61B 5/0507; A61B 5/1116; A61B 5/1118; A61B 5/113; A61B 5/1115; A61B 2562/00; F16M 11/22; F16M 13/02; F16M 13/00; G01K 7/00; H04R 1/026
  USPC ............ 73/866.5, 290 V, 493, 756; 248/542, 248/200–316.8
  See application file for complete search history.

(56) References Cited

U.S. PATENT DOCUMENTS

| | | | |
|---|---|---|---|
| 5,016,873 A | | 5/1991 | Bossa |
| 5,433,416 A | * | 7/1995 | Johnson ............... B65D 23/003 248/475.1 |
| 9,157,619 B1 | * | 10/2015 | Newton ................ F21V 21/116 |
| 2002/0190172 A1 | * | 12/2002 | Oddsen, Jr. ............ F16M 11/24 248/289.11 |
| 2007/0165137 A1 | * | 7/2007 | Lai ........................ F16M 11/08 348/375 |
| 2017/0068149 A1 | * | 3/2017 | Fromm ................ F16M 11/041 |

OTHER PUBLICATIONS

Extended European Search Report dated Apr. 21, 2017 in corresponding European Patent Application No. 16193021.9.
Espacenet Bibliographic data, Chinese Publication No. 104709220 A, published Jun. 17, 2015.

\* cited by examiner

SENSOR MOUNTING BRACKET

CROSS-REFERENCE TO RELATED APPLICATIONS

This present application is based upon and claims the benefit of priority of the prior Japanese Patent Application No. 2015-225973, filed on Nov. 18, 2015, the entire contents of which are incorporated herein by reference.

FIELD

The disclosure is related to a sensor mounting bracket.

BACKGROUND

An mounting bracket for an apparatus is known from Japanese Unexamined Utility Model Application Publication No. 2-74715 (referred to as "Patent Document 1"). The mounting bracket disclosed in Patent Document 1 includes a rotation mechanism around two axes such that an orientation of the apparatus can be changed around the two axes.

According to the conventional technique such as disclosed in Patent Document 1, the rotation mechanism causes a construction of the mounting bracket to be complicated.

SUMMARY

According to one aspect, a sensor mounting bracket is provided, and the sensor mounting bracket includes:

a first plate portion having a first reference part indicative of a first reference direction, and having a first mounting surface that is capable of being attached to either a sensor unit or a wall;

a second plate portion having a second reference part indicative of a second reference direction, and having a second mounting surface that is capable of being attached to either the sensor unit or the wall; and a coupling element fixed to the first and second plate portions, and coupling the first and second plate portions, wherein when X, Y, and Z axes perpendicular to each other are assumed, a second normal vector normal to the second mounting surface has Y and Z components greater than 0 in a first state in which the first reference part is aligned with X direction and the first mounting surface is in XZ plane, and a first normal vector normal to the first mounting surface has Y and Z components greater than 0 in a second state in which the second reference part is aligned with X direction and the second mounting surface is in XZ plane, the first normal vector in the second state being oriented differently from the second normal vector in the first state.

The object and advantages of the embodiment will be realized and attained by means of the elements and combinations particularly pointed out in the claims. It is to be understood that both the foregoing general description and the following detailed description are exemplary and explanatory and are not restrictive of the invention.

DESCRIPTION OF EMBODIMENTS

In the following, embodiments will be described with reference to the accompanying drawings.

First Embodiment

Figure 1:
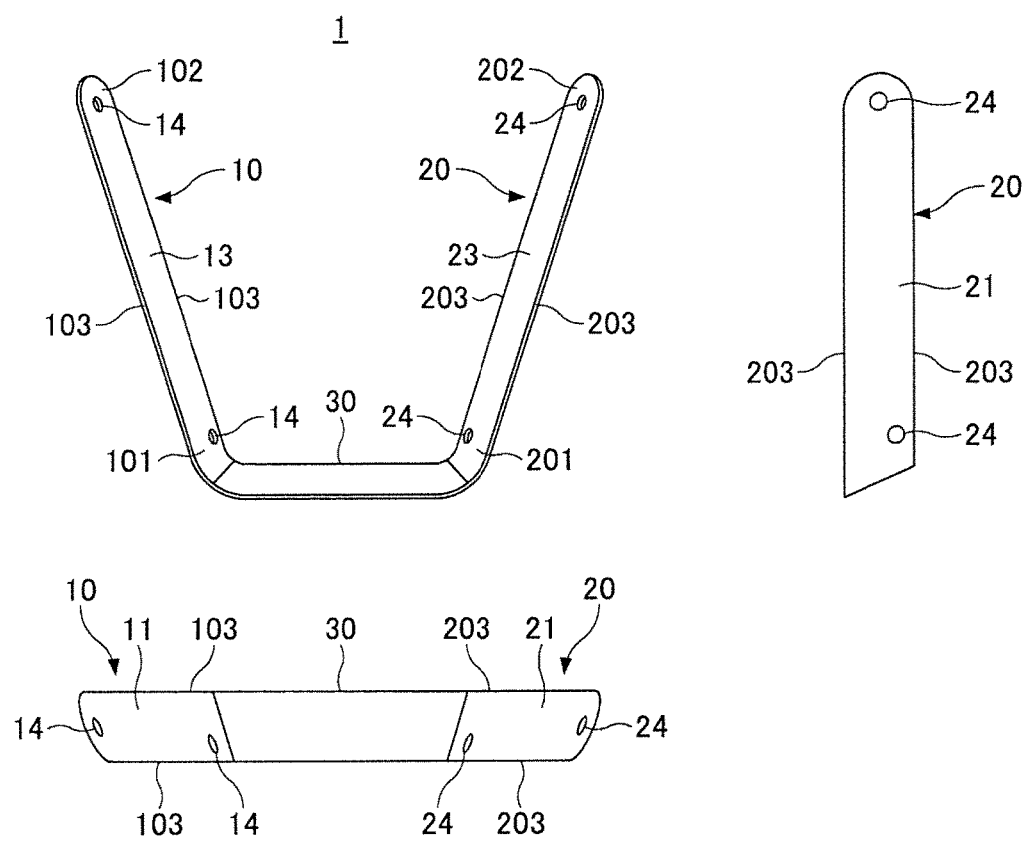
FIG. 1 illustrates three views of an example of a sensor mounting bracket according to a first embodiment.
Figure 2A:
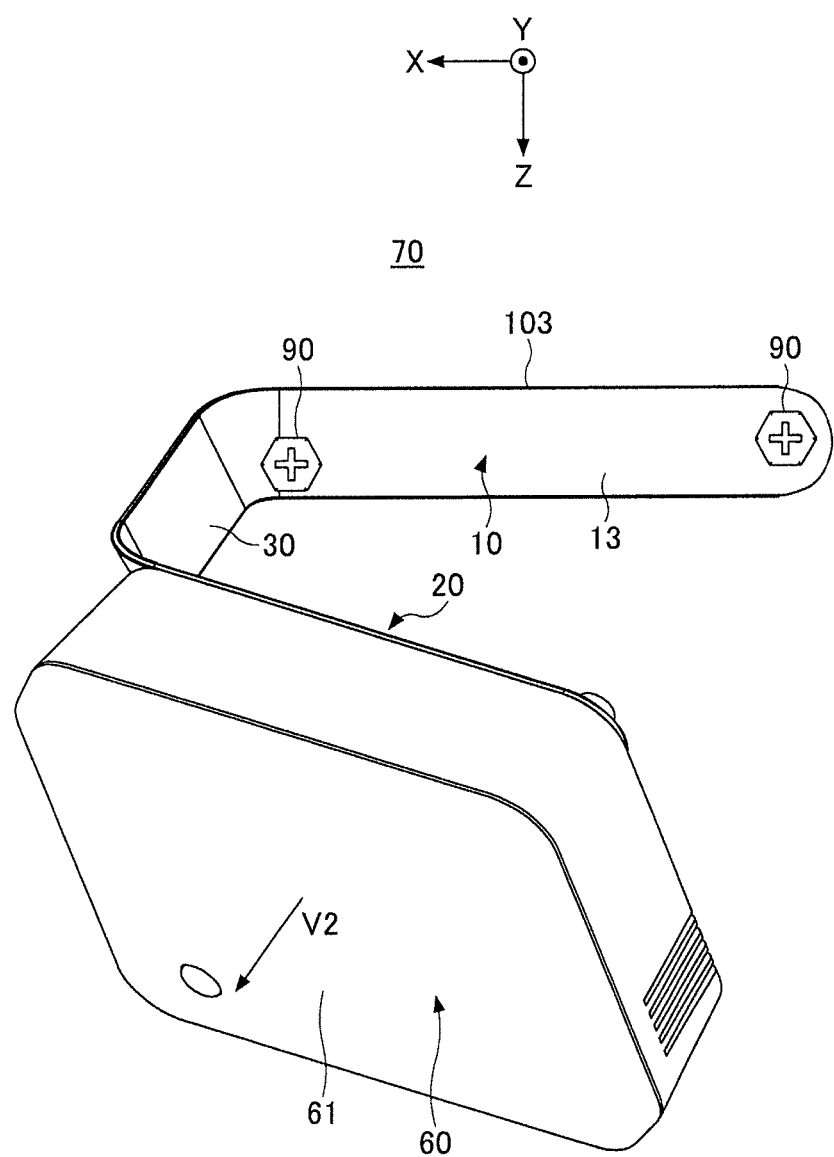
FIG. 2A is a diagram illustrating a first mounting state viewed from a positive side of Y direction.
Figure 2B:
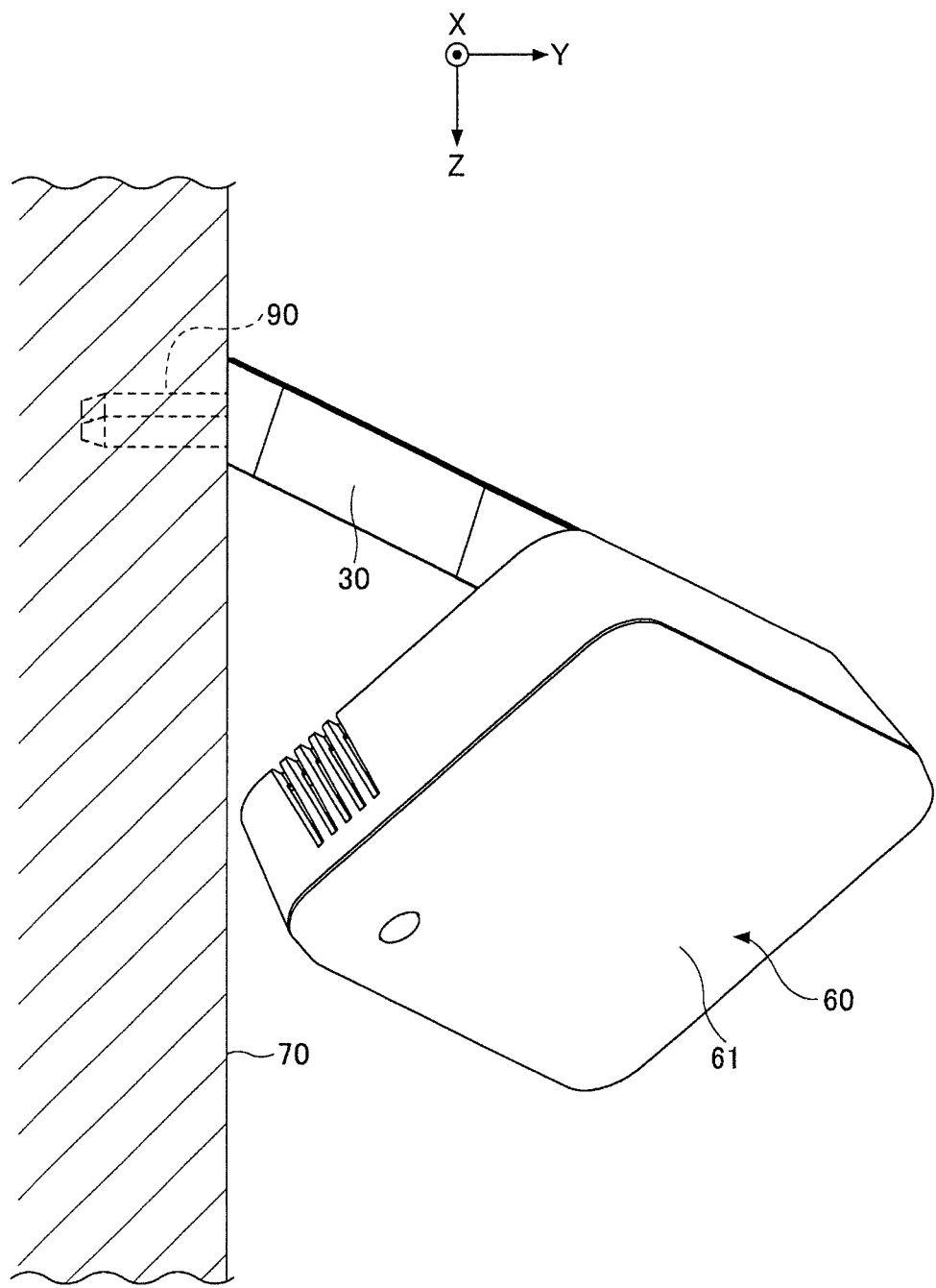
FIG. 2B is a diagram illustrating the first mounting state viewed from a positive side of X direction.
Figure 2C:
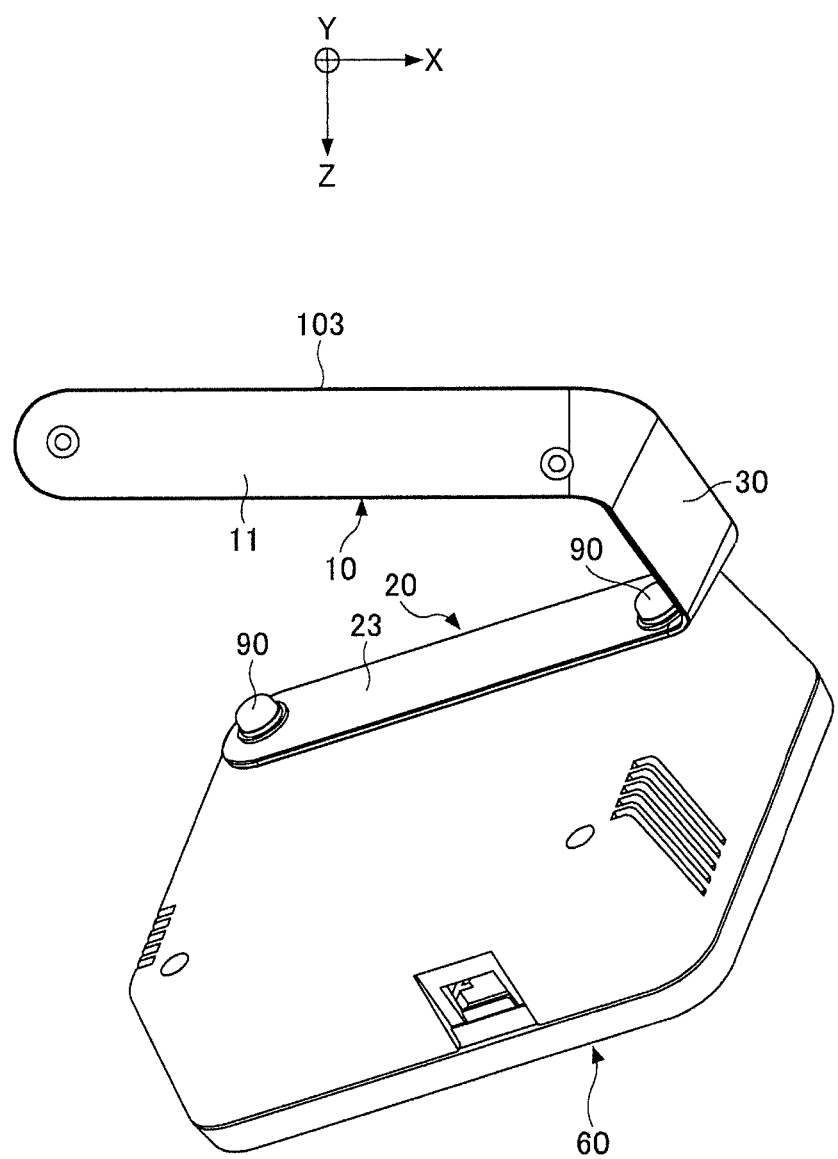
FIG. 2C is a diagram illustrating the first mounting state viewed from a negative side of Y direction.
Figure 3A:
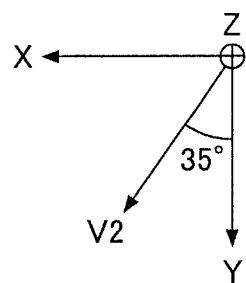
FIG. 3A is a diagram explaining a normal vector V2 of a second mounting surface.
Figure 3B:
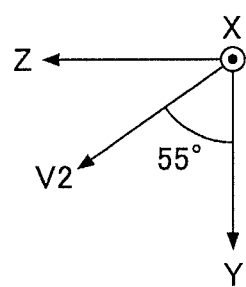
FIG. 3B is a diagram explaining a normal vector V2 of a second mounting surface.
Figure 4A:
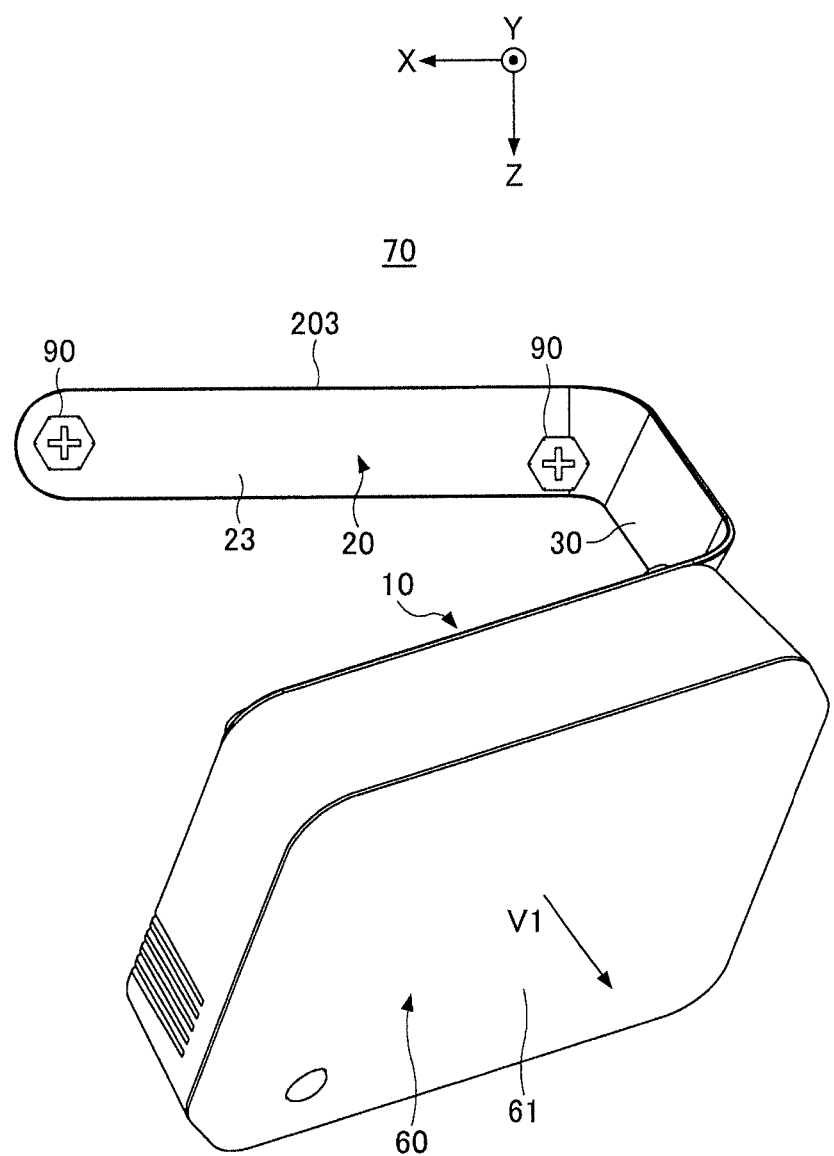
FIG. 4A is a diagram illustrating a second mounting state viewed from a positive side of Y direction.
Figure 4B:
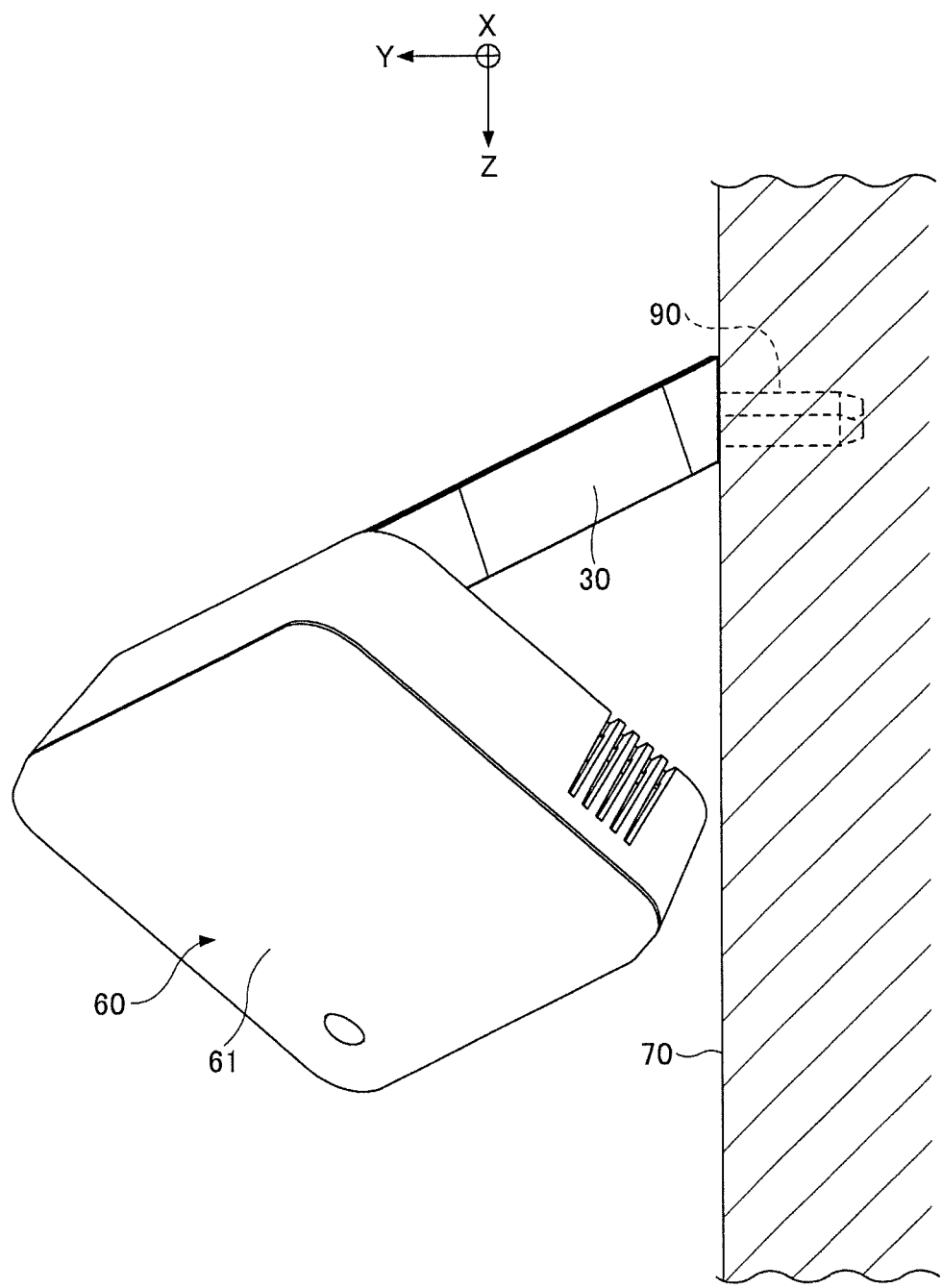
FIG. 4B is a diagram illustrating the second mounting state viewed from a negative side of X direction.
Figure 4C:
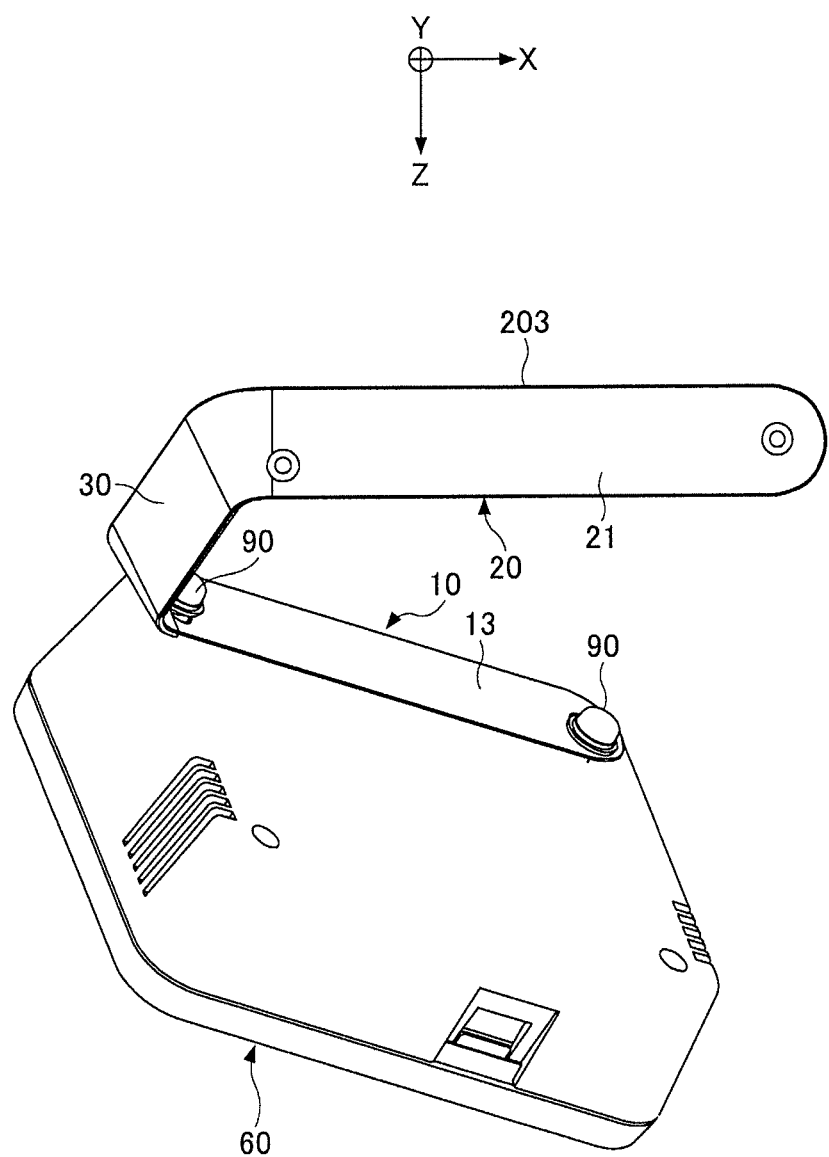
FIG. 4C is a diagram illustrating the second mounting state viewed from a negative side of Y direction.
Figure 5A:
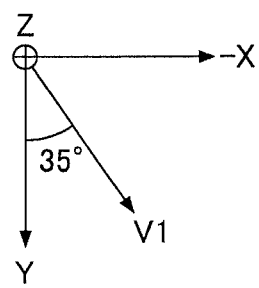
FIG. 5A is a diagram explaining a normal vector V1 of a first mounting surface.
Figure 5B:
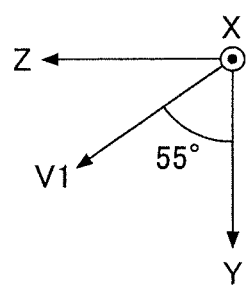
FIG. 5B is a diagram explaining a normal vector V1 of a first mounting surface.

FIG. 1 illustrates three views of an example of a sensor mounting bracket 1 according to a first embodiment. FIGS. 2A through 2C illustrate a first mounting state (an example of a first state) viewed from three directions, respectively. FIG. 3A and FIG. 3B are diagrams explaining a normal vector V2 (an example of a second normal vector) of a second mounting surface 21. FIGS. 4A through 4C illustrate a second mounting state (an example of a second state) viewed from three directions, respectively. FIG. 5A and FIG. 5B are diagrams explaining a first vector V1 (an example of a first normal vector) of a first mounting surface 11.

The sensor mounting bracket 1 is constructed to mount a sensor unit 60 (see FIGS. 2A through 2C, etc.) to a wall.

The sensor unit 60 is used for conditioning air in a room in cooperation with an air conditioner, for example. In this case, the sensor unit 60 includes temperature and humidity sensors that detect temperature and humidity in the room, and an illuminance sensor that detects the illuminance in the room. Further, the sensor unit 60 may include an image sensor or a biological sensor that detects a state of a human(s) in the room. The biological sensor emits radio waves (micro waves, for example) to obtain biological information (activity, breathing, heart beats of the human) based on reflection waves thereof. In this case, the sensor unit 60 can be used in a system for watching over a particular person(s) such as an infant, a patient, or an elder. In the following, as an example, the sensor unit 60 includes the biological sensor that emits the radio waves in the room to obtain biological information based on reflection waves thereof.

The sensor unit 60 includes a mounting surface on a back side thereof that is to be attached to the sensor mounting bracket 1. The mounting surface is flat, for example, and includes a tightening hole (not illustrated) at which a fastener 90 (see FIGS. 2A through 2C, etc.) such as a screw, etc., is tightened. The sensor unit 60 includes a sensing surface 61 on a front side thereof. The biological sensor in the sensor unit 60 emits and receives the radio waves via the sensing surface 61. The biological sensor has directivity. Here, as an example, the biological sensor is configured such that the directivity in a normal direction of the sensing surface 61 is maximized and has a detection range extending concentrically around the normal direction of the sensing surface 61.

The sensor mounting bracket 1 includes a first plate portion 10, a second plate portion 20, and a coupling portion 30, as illustrated in FIG. 1. The sensor mounting bracket 1 is V-shaped as a whole, as illustrated in FIG. 1. The sensor mounting bracket 1 is formed from a metal plate (a sheet metal), for example. The sensor mounting bracket 1 is formed by bending a sheet of the metal plate, for example.

The sensor mounting bracket 1 can implement two types of mounting states according to an environment in which the sensor mounting bracket 1 is to be used. In the first mounting state, as illustrated in FIGS. 2A through 2C, the first plate portion 10 is attached to a wall 70, and the sensor unit 60 is attached to the second plate portion 20. In the second mounting state, as illustrated in FIGS. 4A through 4C, the second plate portion 20 is attached to the wall 70, and the sensor unit 60 is attached to the first plate portion 10. The first and second mounting states are further described hereinafter. Which of the first and second mounting states is to be used depends on the environment, such as a construction of the room, etc., for example, in which the sensor mounting bracket 1 is to be used.

Here, as illustrated in FIGS. 2A through 2C and FIGS. 4A through 4C, three axes X, Y, and Z, which are perpendicular to each other, are assumed. The wall 70 is parallel to XY plane, and a positive side of Z axis corresponds to a downside in a vertical direction.

The first plate portion 10 includes the first mounting surface 11. The first mounting surface 11 is on an opposite side of a surface 13 (referred to as "a back surface 13", hereinafter) that faces the second plate portion 20, as illustrated in FIG. 1. The first mounting surface 11 is flat; however, the first mounting surface 11 may partially include a concave portion, etc., such as a bead, etc., for reinforcement.

The first plate portion 10 extends straight from a first end 101 on the coupling portion 30 side to a second end 102. The second end 102 is a free end. In the following, a longitudinal direction of the first plate portion 10 corresponds to a direction from the first end 101 to the second end 102 (or vice versa), and a width direction of the first plate portion 10 corresponds a direction perpendicular to the longitudinal direction of the first plate portion 10 (and in a plane of the first plate portion 10).

The first plate portion 10 includes a first reference portion 103 indicative of a first reference direction. In the example illustrated in FIG. 1, the first reference portion 103 is defined by edge portions on the opposite sides of the first plate portion 10 in the width direction. The edge portion on the opposite sides of the first plate portion 10 in the width direction extends parallel and straight along the longitudinal. The first reference direction corresponds to the direction in which the first reference portion 103 extends. It is noted that the first reference portion 103 may be defined by a part of the first plate portion 10 along the longitudinal.

The first plate portion 10 includes holes 14 (an example of a first hole) through which the fasteners 90 are passed, respectively. The holes 14 are provided in the first mounting surface 11. The positions and the number of the holes 14 are arbitrary; however, it is preferable that the holes 14 are provided at two or more different locations along the longitudinal direction. In the example illustrated in FIG. 1, the holes 14 are formed at the first end 101 and the second end 102, respectively. Internal threads, with which the fasteners 90 are to be engaged, may be formed in the holes 14. Specifically, the holes 14 may be threaded holes. In this case, the internal threads may be formed in burring portions that are formed by burring processing. It is noted that, if the internal threads are not formed in the holes 14, the holes 14 each have a diameter greater than that of the fastener 90 but smaller than that of a head portion of the fastener 90.

The second plate portion 20 includes the second mounting surface 21. The second mounting surface 21 is on an opposite side of a surface 23 (referred to as "a back surface 23", hereinafter) that faces the first plate portion 10, as illustrated in FIG. 1. The second mounting surface 21 is flat; however, the second mounting surface 21 may partially include a concave portion, etc., such as a bead, etc., for reinforcement.

The second plate portion 20 extends straight from a third end 201 on the coupling portion 30 side to a fourth end 202. The fourth end 202 is a free end. In the following, a longitudinal direction of the second plate portion 20 corresponds to a direction from the third end 201 to the fourth end 202 (or vice versa), and a width direction of the second plate portion 20 corresponds to a direction perpendicular to the longitudinal direction of the second plate portion 20 (and in a plane of the second plate portion 20).

The second plate portion 20 includes a second reference portion 203 indicative of a second reference direction. In the example illustrated in FIG. 1, the second reference portion 203 is defined by edge portions on the opposite sides of the second plate portion 20 in the width direction. The edge portion on the opposite sides of the second plate portion 20 in the width direction extends parallel and straight along the longitudinal. The second reference direction corresponds to the direction in which the second reference portions 203 extends. It is noted that the second reference portion 203 may be defined by a part of the second plate portion 20 along the longitudinal.

The second plate portion 20 includes holes 24 (an example of a second hole) through which the fasteners 90 are passed, respectively. The holes 14 are provided in the second mounting surface 21. The positions and the number of the holes 24 are arbitrary; however, it is preferable that the holes 24 are provided at two or more different locations along the longitudinal direction. In the example illustrated in FIG. 1, the holes 24 are formed at the third end 201 and the fourth end 202, respectively. It is preferable that the holes 24 have the same configuration as the holes 14, respectively.

The coupling portion 30 couples the first plate portion 10 and the second plate portion 20. The coupling portion 30 is fixed to the first end 101 of the first plate portion 10 and the third end 201 of the second plate portion 20. The coupling portion 30 couples the first plate portion 10 and the second plate portion 20 such that the first mounting surface 11 of the first plate portion 10 and the second mounting surface 21 of the second plate portion 20 have a predetermined angle relationship. The predetermined angle relationship is such that the sensing surface 61 of the sensor unit 60 is oriented to a desired direction in either the first mounting state or the second mounting state. The predetermined angle relationship is described in detail with reference to FIGS. 2A through 2C, 3A, 3B, 4A through 4C, 5A, and 5B.

As illustrated in FIGS. 2A through 2C, in the first mounting state, the first mounting surface 11 of the first plate portion 10 (on the back side of the back surface 13 and thus invisible in FIG. 2A) is attached to the wall 70 with a surface contact between the first mounting surface 11 and the wall 70. The attachment of the sensor mounting bracket 1 to the wall 70 can be implemented by the fasteners 90 (wood screws, drill screws with scrape points or sharpen points, for example) through the holes 14 of the first plate portion 10. In the first mounting state, the sensor unit 60 is attached to the second mounting surface 21 of the second plate portion 20. The attachment of the sensor unit 60 in the first mounting state can be implemented by the fasteners 90 (screws, bolts, for example) through the holes 24 of the second plate portion 20, though it is not illustrated.

In the first mounting state, the normal direction of the first mounting surface 11 is parallel to Y axis, as illustrated in FIGS. 2A through 2C. Further, in the first mounting state, the first mounting surface 11 is attached to the wall 70 in such an orientation that the first reference direction (i.e., the first reference portion 103) becomes parallel to X axis. Further, as illustrated in FIGS. 3A and 3B, the normal direction of the second mounting surface 21 of the second plate portion 20 (=the normal direction of the sensing surface 61 of the sensor unit 60) have inclinations with respect to X, Y, and Z axes, respectively. Specifically, when the normal vector V2 of the second mounting surface 21 (in a direction going away from the wall 70) is defined as such V2=(X2, Y2, Z2), the components X2, Y2, and Z2 are all positive values. It is noted that, in the following, the normal vector V2 is defined in a unit vector expression.

Similarly, as illustrated in FIGS. 4A through 4C, in the second mounting state, the second mounting surface 21 of the second plate portion 20 (on the back side of the back surface 23 and thus invisible in FIG. 4A) is attached to the wall 70 with a surface contact between the second mounting surface 21 and the wall 70. The attachment of the sensor mounting bracket 1 to the wall 70 in the second mounting state can be implemented by the fasteners 90 through the holes 24 of the second plate portion 20, as illustrated in FIGS. 4A through 4C. In the second mounting state, the sensor unit 60 is attached to the first mounting surface 11 of the first plate portion 10. The attachment of the sensor unit 60 can be implemented by the fasteners 90 through the holes 14 of the first plate portion 10, though it is not illustrated.

In the second mounting state, the normal direction of the second mounting surface 21 is parallel to Y axis, as illustrated in FIGS. 4A through 4C. Further, in the second mounting state, the second mounting surface 21 is attached to the wall 70 in such an orientation that the second reference direction (i.e., the second reference portion 203) becomes parallel to X axis. Further, the normal direction of the first mounting surface 11 of the first plate portion 10 (=the normal direction of the sensing surface 61 of the sensor unit 60) have inclinations with respect to X, Y, and Z axes, respectively. Specifically, when the normal vector V1 of the first mounting surface 11 (in a direction going away from the wall 70) is defined as such V1=(X1, Y1, Z1), the component X1 is a negative value, and the components Y1 and Z1 are positive values. It is noted that, in the following, the normal vector V1 is defined in a unit vector expression.

Here, the normal vector V2 of the second mounting surface 21 in the first mounting state represents the orientation of the sensing surface 61 of the sensor unit 60 in the first mounting state. Further, the normal vector V1 of the first mounting surface 11 in the second mounting state represents the orientation of the sensing surface 61 of the sensor unit 60 in the second mounting state.

It is preferable that the first vector V1 of the first mounting surface 11 in the second mounting state and the normal vector V2 of the second mounting surface 21 in the first mounting state are symmetric with respect to YZ plane. In other words, preferably, such relationships are met that X1=−X2, Y1=Y2, and Z1=Z2. This means that the orientation of the sensing surface 61 of the sensor unit 60 in the first mounting state and the orientation of the sensing surface 61 of the sensor unit 60 in the second mounting state are symmetric with respect to YZ plane. YZ plane is perpendicular to the surface (XZ plane) of the wall 70. Thus, when the sensor units 60 are attached on the opposite sides in X direction, it becomes possible to assure symmetric sensing regions with respect to YZ plane passing through the center between the sensor units 60 in X direction.

Concrete directions (X1, Y1, Z1), etc., of the first vector V1 and the normal vector V2 are determined according to the environment in which the sensor unit 60 is used, such as a shape, etc., of the room in which the sensor unit 60 is to be used. In the example illustrated in FIGS. 3A and 3B, the normal vector V2 and Y axis have an angle of about 55 degrees when viewed in X direction, and an angle of about 35 degrees when viewed in Z direction. However, these values are just examples, and may be changed within plus and minus 20 degrees, for example, according to the environment (the shape of the room, for example) in which the sensor unit 60 is to be used, as described above. Similarly, in the example illustrated in FIGS. 5A and 5B, the normal vector V1 and Y axis have an angle of about 55 degrees when viewed in X direction, and an angle of about 35 degrees when viewed in Z direction. Similarly, these values are just examples, and may be changed within plus and minus 20 degrees, for example, according to the environment in which the sensor unit 60 is to be used.

According to the sensor mounting bracket 1 of the first embodiment, as illustrated in FIGS. 2A and 4A, the first reference direction (i.e., the first reference portion 103) and the second reference direction (i.e., the second reference portion 203) are parallel to X direction, respectively, in either the first mounting state or the second mounting state. Thus, a worker can use the horizontal direction of the wall 70 as a reference to attach the sensor mounting bracket 1 to the wall 70 with high accuracy. As a result of this, the workability is increased. Further, it becomes possible to reduce the variation (due to the difference of the workers) in the orientation of the sensing surface 61 of the sensor unit 60 attached to the wall 70 in the first mounting state and the second mounting state. The following is based on the premise that the sensor mounting bracket 1 is attached to the wall 70 such that the first or second reference direction is aligned with the horizontal direction of the wall 70.

Further, according to the sensor mounting bracket 1, as illustrated in FIGS. 2A through 2C, and 4A through 4C, the sensing surface 61 of the sensor unit 60 can be oriented in the different directions between the first mounting state and the second mounting state. With this arrangement, it becomes possible to use only one sensor mounting bracket 1 to selectively implement two types of inclined downward directions in which the sensing surface 61 of the sensor unit 60 is oriented. As a result of this, a probability that the sensing surface 61 of the sensor unit 60 can be oriented in the desired inclined downward direction can be increased even if there is a constraint on an attachment positions of the sensor unit 60 due to the construction of the room, etc.

Further, according to the sensor mounting bracket 1, in either the first mounting state or the second mounting state, the normal vector of the sensing surface 61 of the sensor unit 60 can be inclined with respect to X, Y, and Z axes. With this arrangement, it becomes easier to orient the sensing surface 61 of the sensor unit 60 toward the center side of the room even if the attachment position of the sensor unit 60 is limited to the corner of the room (the corner near the ceiling) depending on the structure, etc., of the room. This effect is further explained with reference to FIGS. 6A and 6B.

Figure 6A:
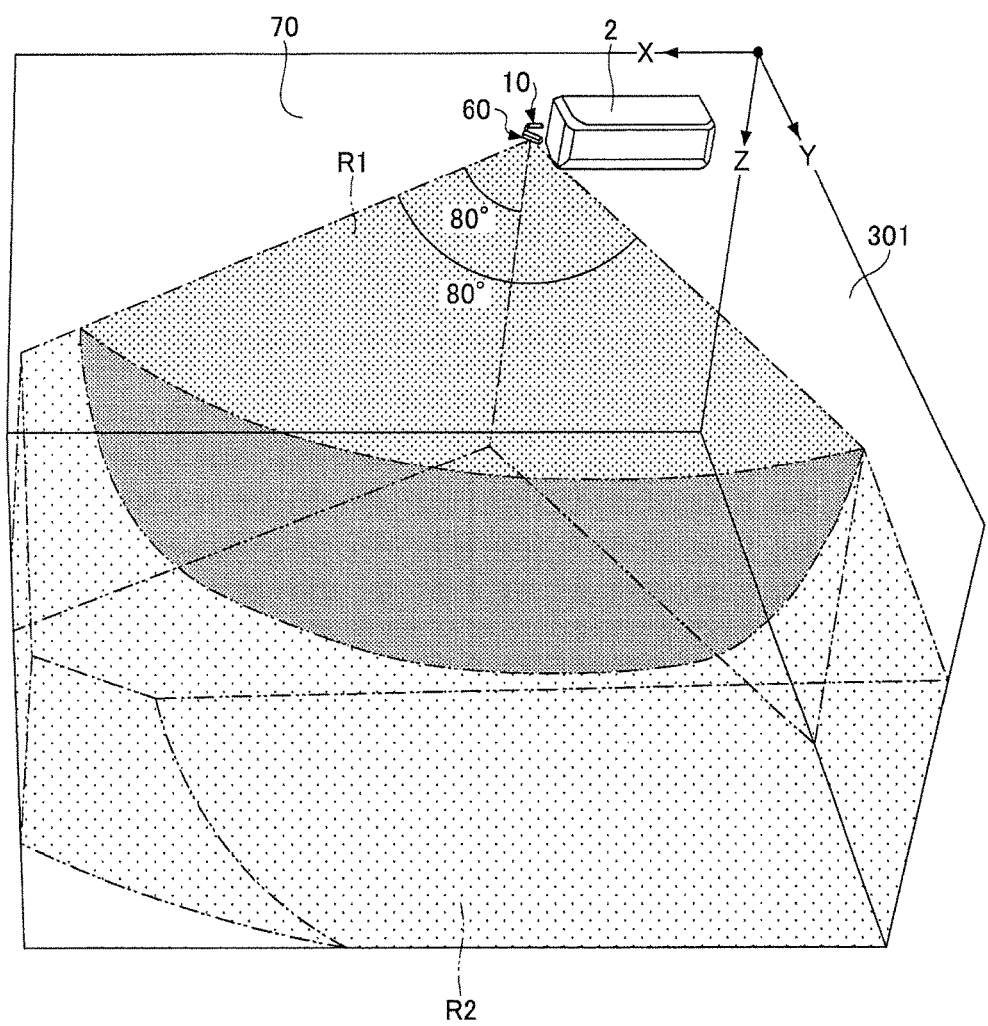
FIG. 6A is a diagram illustrating an example of an installation state of a sensor unit with a sensor mounting bracket 1 in a room.
Figure 6B:
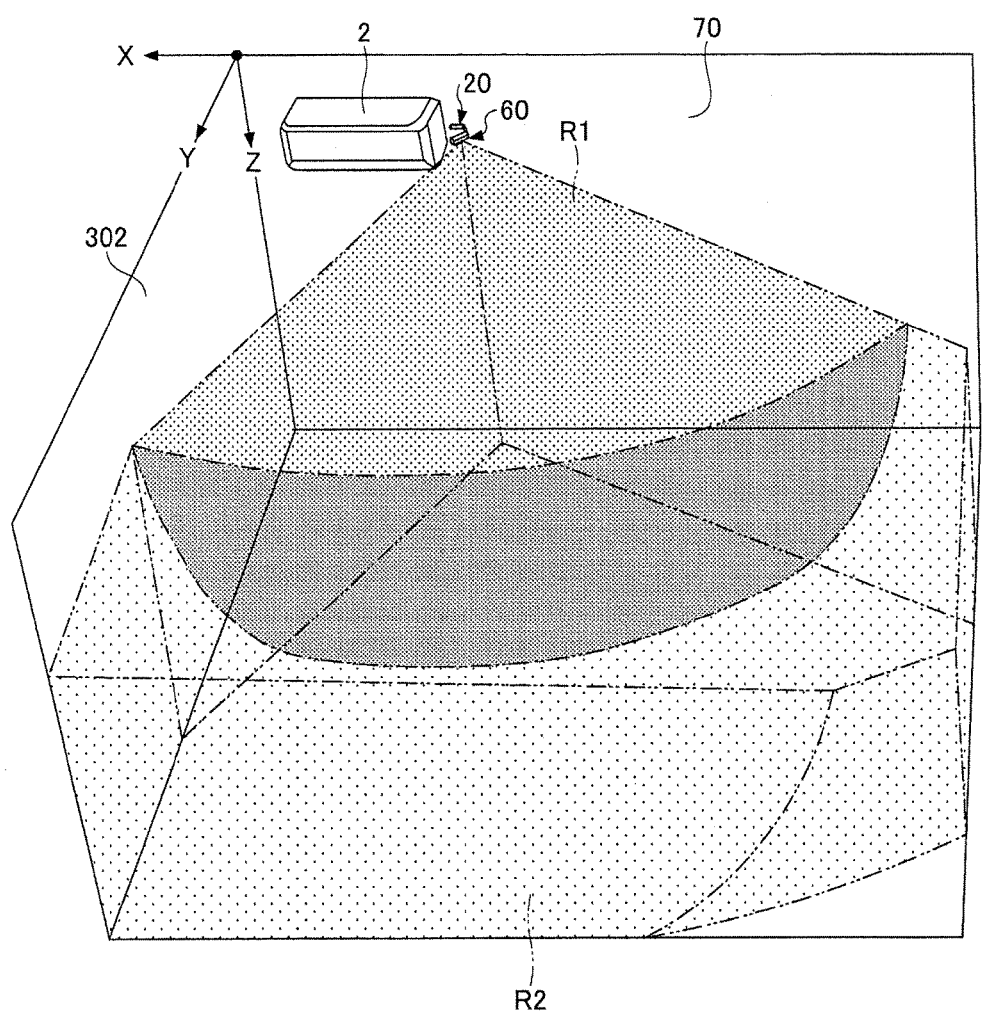
FIG. 6B is a diagram illustrating another example of an installation state of the sensor unit with the sensor mounting bracket 1 in a room.

FIG. 6A is a diagram illustrating an example of an installation state of the sensor unit 60 in the room with the sensor mounting bracket 1. FIG. 6B is a diagram illustrating another example of an installation state of the sensor unit 60 in the room with the sensor mounting bracket 1. FIGS. 6A and 6B are diagrams of the room viewed from the upper side in the inclined direction. In the following explanation, left and right direction, and a depth direction are based on a view point of FIGS. 6A and 6B. In FIGS. 6A and 6B, spaces of the rooms are in a form of a box, and outlines are indicated by lines 301 and 302, respectively. It is noted that, in FIGS. 6A and 6B, X, Y, and Z axes defined in FIGS. 2A through 2C, etc., are illustrated. Further, in FIGS. 6A and 6B, sensing areas of the sensor unit 60 are schematically illustrated with hatched areas R1 and R2. In the examples illustrated in FIGS. 6A and 6B, the sensing area R1 represents an area in which the sensor unit 60 can detect breathing and heart beats of a person(s) who is in the area. Further, the sensing area R2 represents an area in which the sensor unit 60 can detect biological information other than the breathing and the heart beats, such as movements of the person(s) who is in the area. In the examples illustrated in FIGS. 6A and 6B, the sensing area R1 extends over about 180 degrees in the horizontal direction and about 80 degrees in the downward direction. The range of the sensing areas R1 and R2 occupied in the room is determined depending on radio wave strength of the sensor unit 60 and the orientation of the sensing surface 61.

In the example illustrated in FIG. 6A, an air conditioner 2 is provided near the corner of the right farther side. In other words, the air conditioner 2 is provided at a right and upper position of the wall 70 on a further side. The sensor unit 60 is disposed near the air conditioner 2 due to the constraint on wiring routing, etc. For this reason, In the example illustrated in FIG. 6A, like the air conditioner 2, the sensor unit 60 is provided near the corner of the right farther side. In this case, as illustrated in FIG. 6A, the first mounting state is selected. Therefore, the sensor unit 60 has the normal vector of the sensing surface 61 oriented to the center side of the room even through the sensor unit 60 is provided near the corner of the right farther side of the room. Specifically, because the normal vector (X2, Y2, Z2) of the sensing surface 61 is such that X2, Y2, and Z2 are positive values, as described above, the normal vector (X2, Y2, Z2) can be oriented to the center side (left side) of the room in comparison with a case where the normal vector is (0, Y2, Z2), for example. In this way, according to the sensor mounting bracket 1, it becomes easier to assure the sensing area on the left side of the room by adopting the first mounting state even if the air conditioner 2 is provided near the corner of the right farther side of the room.

In the example illustrated in FIG. 6B, an air conditioner 6 is provided near the corner of the left farther side. In other words, the air conditioner 2 is provided at a left and upper position of the wall 70 on a further side. The sensor unit 60 is disposed near the air conditioner 2 due to the constraint on wiring routing, etc. For this reason, In the example illustrated in FIG. 6B, like the air conditioner 2, the sensor unit 60 is provided near the corner of the left farther side. In this case, as illustrated in FIG. 6B, the second mounting state is selected. Therefore, the sensor unit 60 has the normal vector of the sensing surface 61 oriented to the center side of the room even through the sensor unit 60 is provided near the corner of the left farther side of the room. Specifically, because the normal vector (X1, Y1, Z1) of the sensing surface 61 in the second mounting state is such that X1 is a negative value and Y2 and Z2 are positive values, as described above. Thus, the normal vector (X1, Y1, Z1) in the second mounting state can be oriented to the center side (right side) of the room in comparison with a case where the normal vector is (0, Y1, Z1), for example. In this way, according to the sensor mounting bracket 1, it becomes easier to assure the sensing area on the right side of the room by adopting the second mounting state even if the air conditioner 2 is provided near the corner of the left farther side of the room.

In general, neighboring apartment house units in the right and left direction tend to have arrangement of rooms symmetrical in the right and left direction. When the arrangement of rooms is symmetrical in the right and left direction, the attachment positions of the air conditioners 2 also tend to be symmetrical in the right and left direction, correspondingly, as illustrated in FIGS. 6A and 6B.

According to the sensor mounting bracket 1, as described above, the orientation of the sensing surface 61 of the sensor unit 60 in the first mounting state and the orientation of the sensing surface 61 of the sensor unit 60 in the second mounting state are symmetric with respect to YZ plane. In this case, YZ plane corresponds to a partition wall between two neighboring apartment house units, as illustrated in FIGS. 6A and 6B. Thus, the sensor mounting bracket 1 is suited for the attachments of the sensor units 60 in the apartment whose house units have symmetrical arrangement of rooms in the right and left direction, in particular.

Here, the sensor mounting bracket 1 is secured to the wall 70 with the fasteners 90, as described above. The fasteners 90 are fastened from the back surface 13 or 23 side. Thus, when the sensor mounting bracket 1 is secured to the wall 70 with the fasteners 90, the second plate portion 20 or the first plate portion 10, which is located on the back surface 13 or 23 side, may interfere with the fastening work. For example, in order to implement the first mounting state, the fastening work for the fastener 90 from the back surface 13 side is required, and the second plate portion 20 may interfere with the fastening work. Further, the sensor unit 60 is secured to the sensor mounting bracket 1 with the fasteners 90, as described above. The fasteners 90 are fastened from the back surface 13 or 23 side. Thus, when the sensor unit 60 is secured to the sensor mounting bracket 1 with the fasteners 90, the second plate portion 20 or the first plate portion 10 may interfere with the fastening work.

Concerning this, according to the sensor mounting bracket 1, as illustrated in FIG. 2A, the back surface 13 as a whole (and thus the holes 14 themselves) is visible when viewed in Y direction in the first mounting state. Similarly, according to the sensor mounting bracket 1, as illustrated in FIG. 4A, the back surface 23 as a whole (and thus the holes 24 themselves) is visible when viewed in Y direction in the second mounting state. In other words, according to the sensor mounting bracket 1, the coupling portion 30 couples the first plate portion 10 and the second plate portion 20 such that the holes 14 and 24 are visible when viewed in Y direction in either first mounting state or the second mounting state. Thus, according to the sensor mounting bracket 1, in implementing the first mounting state, the fastening work of the fastener 90 from the back surface 13 side is not substantially interfered with by the second plate portion 20, which increases the workability. Similarly, according to the sensor mounting bracket 1, in implementing the second mounting state, the fastening work of the fastener 90 from the back surface 23 side is not substantially interfered with by the first plate portion 10, which increases the workability.

It is noted that according to the sensor mounting bracket 1 of the first embodiment, the back surface 13 as a whole is visible when viewed in Y direction in the first mounting state, and the back surface 23 as a whole is visible when viewed in Y direction in the second mounting state; however, this is not indispensable. For example, the coupling portion 30 may couple the first plate portion 10 and the second plate portion 20 such that circle areas with a predetermined radius around the holes 14 and 24 are visible when viewed in Y direction in either the first mounting state or the second mounting state. In this case, the predetermined radius may be determined based on the radius of a screwdriver tool (an ordinary driver, for example) to be used to fasten the fastener 90. Further, in order to increase the workability, it is preferable that there is a distance between the holes 14 of the first plate portion 10 and the second plate portion 20 such that the screwdriver tool can be inserted, and there is a distance between the holes 24 of the second plate portion 20 and the first plate portion 10 such that the screwdriver tool can be inserted.

Figure 7A:
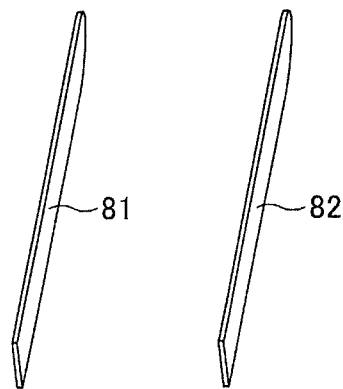
FIG. 7A is a diagram conceptually explaining a way of manufacturing the sensor mounting bracket 1 according to the first embodiment.
Figure 7B:
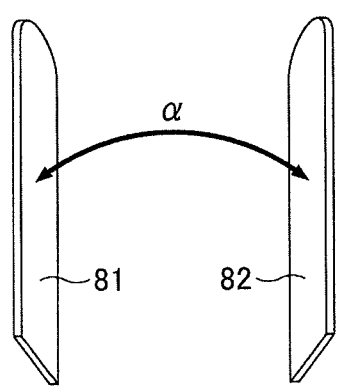
FIG. 7B is a diagram conceptually explaining a way of manufacturing the sensor mounting bracket 1 according to the first embodiment.
Figure 7C:
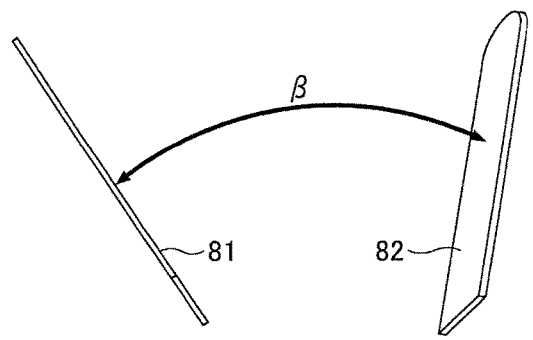
FIG. 7C is a diagram conceptually explaining a way of manufacturing the sensor mounting bracket 1 according to the first embodiment.

Next, with reference to FIGS. 7A through 7C, a way of manufacturing the sensor mounting bracket 1 according to the first embodiment is described.

FIGS. 7A through 7C are diagrams conceptually explaining a way of manufacturing the sensor mounting bracket 1 according to the first embodiment. FIG. 7A conceptually illustrates a state before bending formation. In FIG. 7A, in order to conceptually illustrate a bending direction, a first portion 81 and a second portion 82, which are in the same plane before the bending formation, are conceptually illustrated such that the first portion 81 and the second portion 82 are opposed to each other. FIG. 7B is a diagram explaining the bending formation at a first time, and FIG. 7C is a diagram explaining the bending formation at a second time. In FIGS. 7A through 7C, the first portion 81 is a portion to be the first plate portion 10, and the second portion 82 is a portion to be the second plate portion 20. In FIGS. 7A through 7C, the illustration of a portion to be the coupling portion 30 is omitted.

Before the bending formation, the first portion 81 and the second portion 82 are in the same plane with respect to the portion (not illustrated) to be the coupling portion 30. In other words, the sensor mounting bracket 1 is formed from a sheet metal. It is noted that the sheet metal may be subject to punching (stamping) for the holes 14 and 24 before the bending formation described hereinafter. At first, according to the bending formation at the first time, as illustrated in FIG. 7B, the first portion 81 and the second portion 82 are bent by a predetermined angle α in such a direction that a distance between opposed surfaces (on edge sides) of the first portion 81 and the second portion 82 are increased with respect to a state illustrated in FIG. 7A. It is noted that the predetermined angle α is determined according to the assumed usage environment; however, the predetermined angle α may be 50 degrees plus and minus 15 degrees, for example. Then, according to the bending formation at the second time, as illustrated in FIG. 7C, the first portion 81 and the second portion 82 are bent by a predetermined angle β such that a distance between the free ends of the first portion 81 and the second portion 82 are increased with respect to a state illustrated in FIG. 7B. It is noted that the predetermined angle β is determined according to the assumed usage environment; however, the predetermined angle α may be 35 degrees plus and minus 10 degrees, for example.

According to the examples illustrated in FIGS. 7A through 7C, the sensor mounting bracket 1 can be formed by performing the bending formation twice. The bending formation thus performed twice causes the first mounting surface 11 of the first plate portion 10 and the second mounting surface 21 of the second plate portion 20 to have the predetermined angle relationship described above.

Second Embodiment

Figure 8:
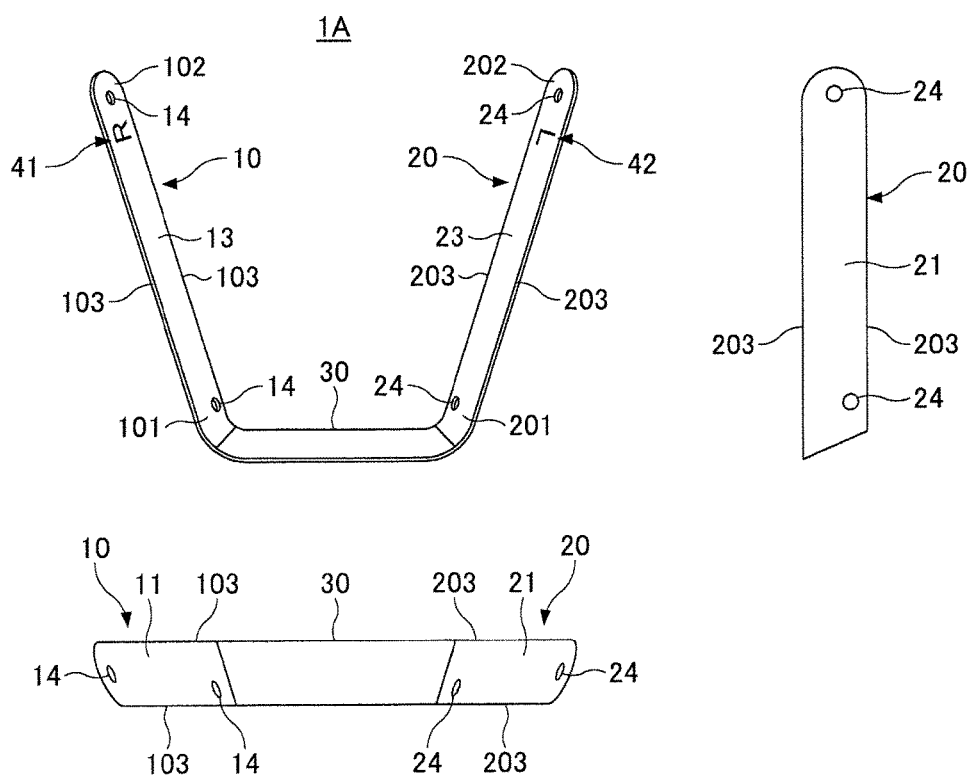
FIG. 8 illustrates three views of an example of a sensor mounting bracket according to a second embodiment.
Figure 9A:
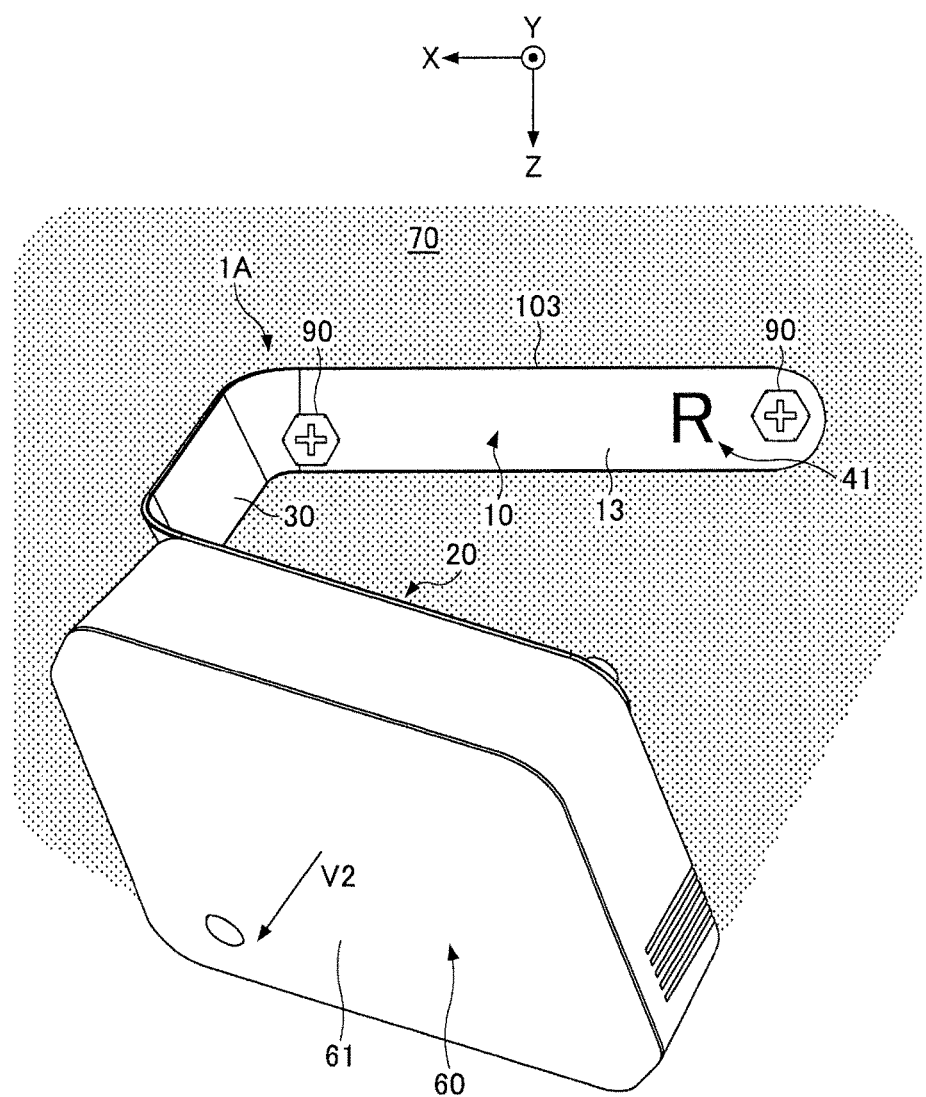
FIG. 9A is a diagram illustrating the first mounting state.
Figure 9B:
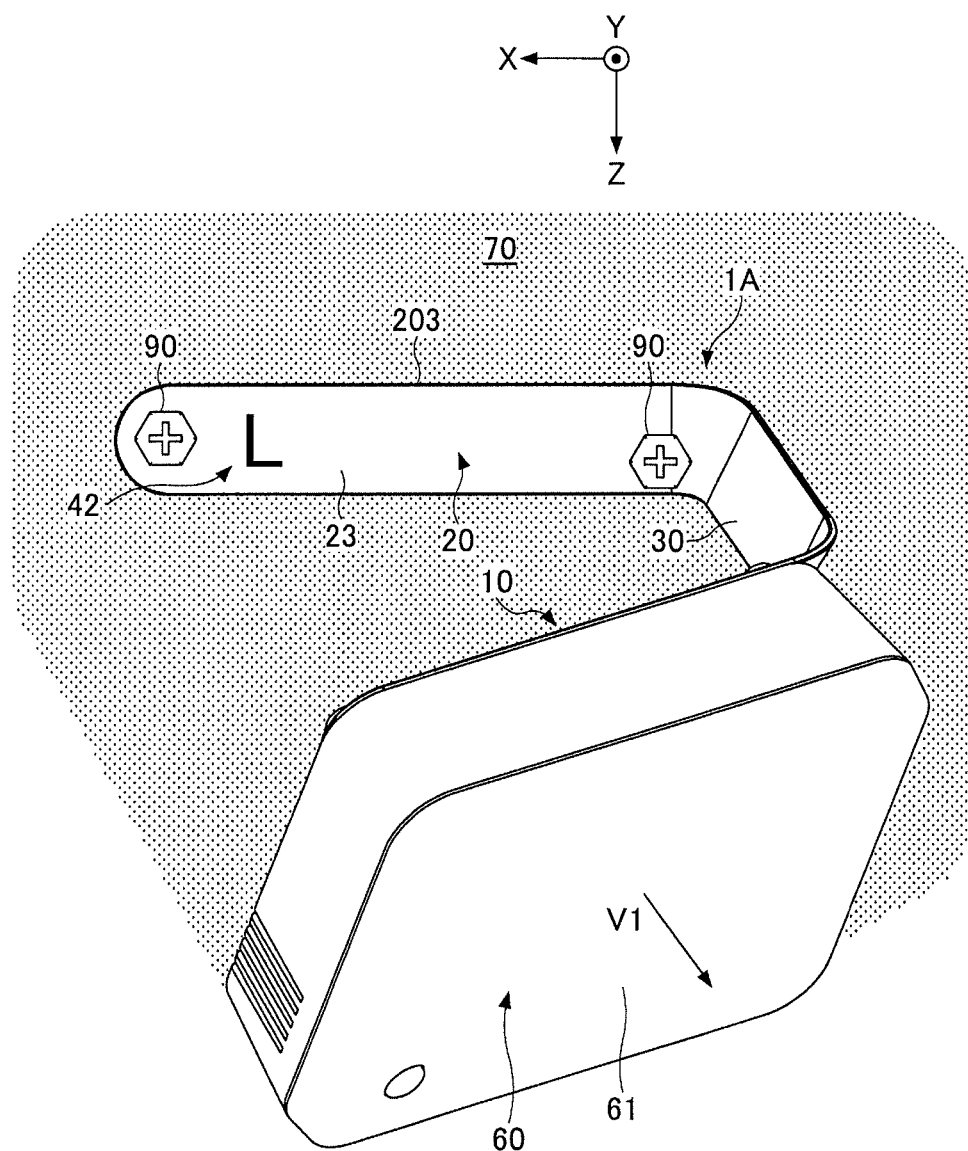
FIG. 9B is a diagram illustrating the second mounting state.

FIG. 8 illustrates three views of an example of a sensor mounting bracket 1A according to a second embodiment. FIG. 9A is a diagram illustrating a first mounting state. FIG. 9B is a diagram illustrating a second mounting state.

The sensor mounting bracket 1A according to the second embodiment differs from the sensor mounting bracket 1 according to the first embodiment in that a first discrimination mark 41 and a second discrimination mark 42 are given, and other configuration may be the same. Elements that may be the same as those according to the first embodiment are given the same reference numbers in FIG. 8, and an explanation thereof is omitted.

The first discrimination mark 41 is given to the back surface 13 (i.e. the back side surface of the first mounting surface 11) of the first plate portion 10. The first discrimination mark 41 may be formed by marking, for example. Such marking can be implemented at the forming process with dies.

The first discrimination mark 41 includes information for supporting work for the attachment of the sensor unit 60 to the wall 70. The first discrimination mark 41 functions at the time of the work for the attachment to implement the first mounting state illustrated in FIG. 9A. Specifically, the first discrimination mark 41 includes a character suggesting "right". In the example illustrated in FIG. 8, the first discrimination mark 41 includes a character "R". This is because the first mounting state, as illustrated in FIG. 6A, is used to attach the sensor unit 60 on the right side (near the right corner) of the room. With this arrangement, the worker can see the first discrimination mark 41 at the fastening work for the attachment on the right side of the room with the fasteners 90, and thus determine whether the currently performing work is correct, as illustrated in FIG. 9A. As a result of this, the workability is increased, and attachment errors (the second mounting state is erroneously implemented when the first mounting state is to be implemented) can be reduced.

Similarly, the second discrimination mark 42 includes information for supporting work for the attachment of the sensor unit 60 to the wall 70. The second discrimination mark 42 includes information different from the first discrimination mark 41. Specifically, the second discrimination mark 42 includes a character suggesting "left". In the example illustrated in FIG. 8, the second discrimination mark 42 includes a character "L". This is because the second mounting state, as illustrated in FIG. 6B, is used to attach the sensor unit 60 on the left side (near the left corner) of the room. With this arrangement, the worker can see the second discrimination mark 42 at the fastening work for the attachment on the left side of the room with the fasteners 90, and thus determine whether the currently performing work is correct, as illustrated in FIG. 9B. As a result of this, the workability is increased, and attachment errors (the first mounting state is erroneously implemented when the second mounting state is to be implemented) can be reduced.

Third Embodiment

Figure 10A:
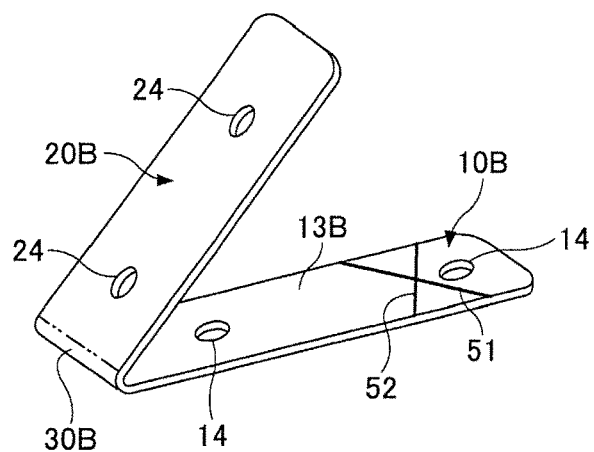
FIG. 10A illustrates a perspective view of an example of a sensor mounting bracket according to a third embodiment.
Figure 10B:
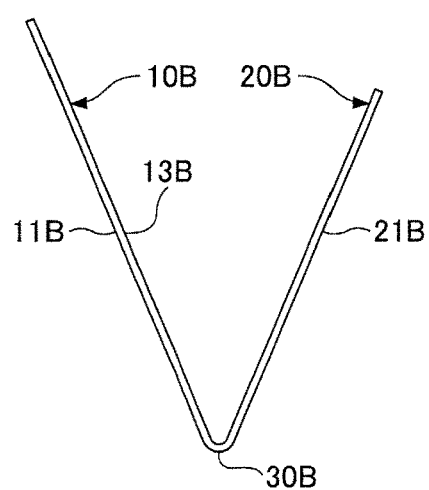
FIG. 10B illustrates a side view of an example of the sensor mounting bracket according to the third embodiment.
Figure 11A:
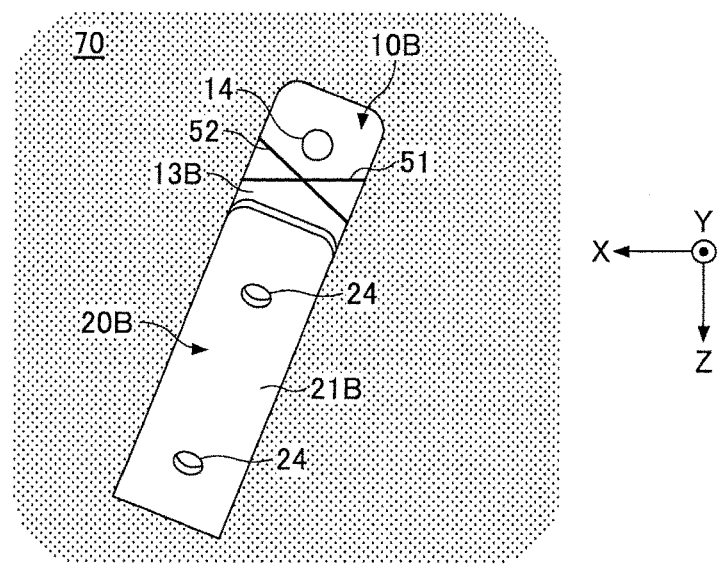
FIG. 11A is a diagram conceptually illustrating the first mounting state.
Figure 11B:
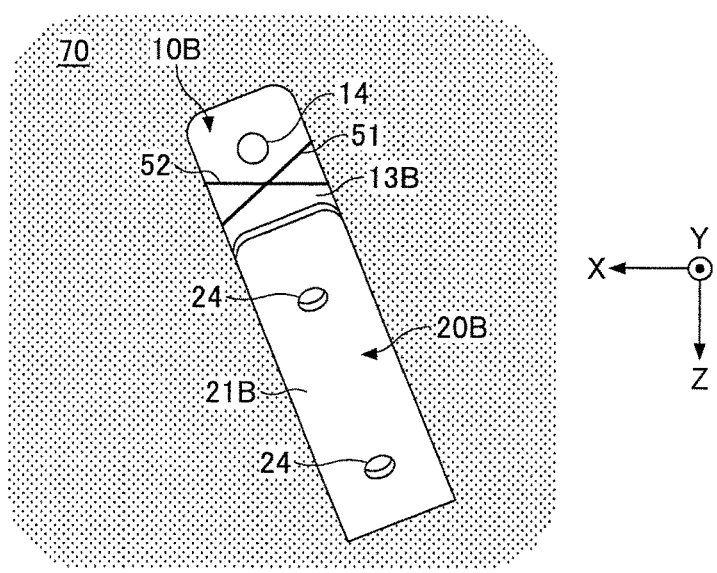
FIG. 11B is a diagram conceptually illustrating the second mounting state.

FIG. 10A illustrates a perspective view of an example of a sensor mounting bracket 1B according to a third embodiment. FIG. 10B illustrates a side view of an example of the sensor mounting bracket 1B. FIG. 11A is a diagram conceptually illustrating the first mounting state. FIG. 11B is a diagram conceptually illustrating the second mounting state. In FIGS. 11A and 11B, an illustration of the sensor unit 60 and the fasteners 90 is omitted.

In the following explanation, elements (the sensor unit 60, for example) that are the same as those in the first embodiment described above are given reference numbers.

The sensor mounting bracket 1B includes a first plate portion 10B, a second plate portion 20B, and a coupling portion 30B. The sensor mounting bracket 1B can be formed by bending a flat sheet metal in such a direction that ends of the sheet metal on opposite sides come close to each other. The sensor mounting bracket 1B is formed without performing the bending formation twice, unlike the sensor mounting bracket 1 according to the first embodiment described above.

The first plate portion 10B includes a first mounting surface 11B which can be attached to the wall 70 of the room. A first reference direction and a second reference direction are marked on a back surface 13B of the first mounting surface 11B, as illustrated in FIG. 10A. In other words, the first plate portion 10B includes, on the back surface 13B, a first mark portion 51 related to the first reference direction and a second mark portion 52 related to the second reference direction. The first reference direction and the second reference direction intersect with each other in an inclined direction, as illustrated in FIG. 10A. The first plate portion 10B includes holes 14 formed therein through which the fasteners 90 pass.

The second plate portion 20B includes a second mounting surface 21B which can be attached to the sensor unit 60. The second plate portion 20B includes holes 24 formed therein through which the fasteners 90 pass.

Here, X, Y, and Z axes, which are the same as those in the first embodiment, are assumed. The sensor mounting bracket 1B can implement two types of mounting states according to a way in which the sensor mounting bracket 1 is to be used.

As illustrated in FIG. 11A, in the first mounting state, the first mounting surface 11B of the first plate portion 10B (on the back side of the back surface 13B and thus invisible in FIG. 11A) is attached to the wall 70 with a surface contact between the first mounting surface 11B and the wall 70. In the first mounting state, the first mounting surface 11B is attached to the wall 70 in such an orientation that the first reference direction (i.e., the first mark portion 51) becomes parallel to X axis. In the first mounting state, the normal direction of the second mounting surface 21B of the second plate portion 20B (=the normal direction of the sensing surface 61 of the sensor unit 60) is the same as the normal direction of the second mounting surface 21 in the first mounting state according to the first embodiment described above.

As illustrated in FIG. 11B, in the second mounting state, the first mounting surface 11B of the first plate portion 10B (on the back side of the back surface 13B and thus invisible in FIG. 11A) is attached to the wall 70 with a surface contact between the first mounting surface 11B and the wall 70. In the second mounting state, the first mounting surface 11B is attached to the wall 70 in such an orientation that the second reference direction (i.e., the second mark portion 52) becomes parallel to X axis. In the second mounting state, the normal direction of the second mounting surface 21B of the second plate portion 20B (=the normal direction of the sensing surface 61 of the sensor unit 60) is the same as the normal direction of the first mounting surface 11 in the second mounting state according to the first embodiment described above.

Thus, according to the third embodiment, the same effects as the first embodiment described above can be obtained. In particular, according to the third embodiment, the first mark portion 51 and the second mark portion 52 erase the necessity of the combination of the bending processes, which is advantageous in terms of manufacturing. On the other hand, the work for aligning the first mark portion 51 and the second mark portion 52 with the horizontal direction of the wall 70 requires slightly more skill than the work for aligning the first reference portion 103 and the second reference portion 203 according to the first embodiment with the horizontal direction of the wall 70.

It is noted that, in the third embodiment, discrimination marks corresponding to the first discrimination mark 41 and the second discrimination mark 42 may be given to the first mark portion 51 and the second mark portion 52, respectively, as is the case with the second embodiment described above. As a result of this, the workability is increased, and attachment errors (the first mounting state is erroneously implemented when the second mounting state is to be implemented, or vice versa) can be reduced.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention. Further, all or part of the components of the embodiments described above can be combined.

For example, according to the first and second embodiments, the sensor mounting brackets 1 and 1A are secured to the wall 70 with the fasteners 90 and the sensor units 60 are secured to the sensor mounting brackets 1 and 1A with the fasteners 90; however, this is not indispensable. For example, the sensor mounting brackets 1 and 1A may be adhered to the wall 70 with adhesive tapes with releasing papers, and the sensor units 60 may be adhered to the sensor mounting brackets 1 and 1A with adhesive tapes with releasing papers. In this case, the holes 14 and 24 become unnecessary, and the adhesive tapes with the releasing papers (i.e., double-sided tapes) are adhered to the first mounting surface 11 and the second mounting surface 21, respectively.

Further, according to the first and second embodiments, the normal directions of the first mounting surface 11 and the second mounting surface 21 have relationships such that the normal directions of the first mounting surface 11 and the second mounting surface 21 are equal to the normal directions of the sensing surfaces 61 of the sensor units 60 attached to the first mounting surface 11 and the second mounting surface 21, respectively. However, this is not indispensable. Specifically, the normal directions of the first mounting surface 11 and the second mounting surface 21 may have predetermined offsets (deviations) with respect to the normal directions of the sensing surfaces 61 of the sensor units 60 attached to the first mounting surface 11 and the second mounting surface 21, respectively. Such offsets occur in the case where the sensing surface 61 of the sensor unit 60 is not parallel to the mounting surface of the sensor unit 60, etc., for example. In this case, the predetermined offsets may be considered to determine the normal direction of the second mounting surface 21 in the first mounting state and the normal direction of the first mounting surface 11 in the second mounting state.

Further, according to the first and second embodiments, the first reference portion 103 is implemented by the edges portion of the first plate portion 10 on the opposite sides in the width direction, and the second reference portion 203 is implemented by the edges portion of the second plate portion 20 on the opposite sides in the width direction; however, this is not indispensable. For example, the first reference direction may be marked on the back surface 13 of the first plate portion 10, and the second reference direction may be marked on the back surface 23 of the second plate portion 20. In this case, the first reference portion 103 is a straight mark portion on the back surface 13 of the first plate portion 10, and the second reference portion 203 is a straight mark portion on the back surface 23 of the second plate portion 20. In this case, the edges portion of the first plate portion 10 on the opposite sides in the width direction do not necessarily extend in the first reference direction, and the edges portion of the second plate portion 10 on the opposite sides in the width direction do not necessarily extend in the second reference direction.

Further, according to the first and second embodiments, the first reference portion 103 and the second reference portion 203 are to be aligned with the horizontal direction (X axis) of the wall 70; however, the sensor mounting bracket may be formed such that the sensor mounting bracket has reference portions to be aligned with the vertical direction (Z axis) of the wall 70.

What is claimed is:

1. A sensor mounting bracket attached to a wall and a sensor unit, comprising:
a first plate portion having a first reference part indicative of a first reference direction, and having a first mounting surface that is attached to the wall in a first state and attached to the sensor unit in a second state;
a second plate portion having a second reference part indicative of a second reference direction, and having a second mounting surface that is attached to the sensor unit in the first state and attached to the wall in the second state; and
a coupling portion fixed to the first and second plate portions to couple the first and second plate portions, wherein
when X, Y, and Z axes perpendicular to each other are assumed,
a second normal vector normal to the second mounting surface has Y and Z components greater than 0 and has an inclination with respect to each of X, Y, and Z axes in the first state in which the first reference part is aligned with X direction and the first mounting surface is in XZ plane, and
a first normal vector normal to the first mounting surface has Y and Z components greater than 0 and has an inclination with respect to each of X, Y, and Z axes in the second state in which the second reference part is aligned with X direction and the second mounting surface is in XZ plane, the first normal vector in the second state being oriented differently from the second normal vector in the first state.

2. The sensor mounting bracket attached to the wall and the sensor unit of claim 1, wherein the coupling portion is fixed to the first plate portion at an end of the first plate portion in the first reference direction and the second plate portion at an end of the second plate portion in the second reference direction, and
in the first state the first reference part is parallel with X direction, in the second state the second reference part is parallel with X direction, and a direction from the end to the other end of the first plate portion in the first state is opposite to a direction from the end to the other end of the second plate portion in the second state.

3. The sensor mounting bracket attached to the wall and the sensor unit of claim 2, wherein when it is defined such that a positive side of X direction corresponds to the direction from the end to the other end of the first plate portion in the first state, and a positive side of Y direction corresponds to a side of the second plate portion with respect to the first plate portion in the first state,
the second normal vector in the first state has respective components of X, Y, and Z direction whose signs are positive, and
the first normal vector in the second state has a component of X direction whose sign is negative, and components of Y and Z direction whose signs are positive.

4. The sensor mounting bracket attached to the wall and the sensor unit of claim 3, wherein an orientation of the second mounting surface in the first state and an orientation of the first mounting surface in the second state are symmetrical with respect to YZ plane.

5. The sensor mounting bracket attached to the wall and the sensor unit of claim 3, wherein the first plate portion includes a first edge extending straight,
the first reference part is the first edge,
the second plate portion includes a second edge extending straight, and
the second reference part is the second edge.

6. The sensor mounting bracket attached to the wall and the sensor unit of claim 3, wherein the first plate part includes a first hole through which a fastening element passes, and
the second plate part includes a second hole through which a fastening element passes.

7. The sensor mounting bracket attached to the wall and the sensor unit of claim 6, wherein the coupling portion couples the first and second plate portions such that the first hole is visible in Y direction in the first state and the second hole is visible in Y direction in the second state.

8. The sensor mounting bracket attached to the wall and the sensor unit of claim 6, wherein the first hole and the second hole have internal threads formed therein.

9. The sensor mounting bracket attached to the wall and the sensor unit of claim 8, wherein the internal threads are formed in burring portions.

10. The sensor mounting bracket attached to the wall and the sensor unit of claim 3, wherein the first plate portion includes a back surface on a back side of the first mounting surface, the back surface having a first identification mark, and the second plate portion includes a back surface on a back side of the second mounting surface, the back surface having a second identification mark different from the first identification mark.

11. The sensor mounting bracket attached to the wall and the sensor unit of claim 1, wherein the first plate portion includes a first end fixed to the coupling portion and a second end that is a free end, the second plate portion includes a third end fixed to the coupling portion and a fourth end that is a free end, a direction from the first end to the second end in the first state is opposite to a direction from the third end to the fourth end in the second state.

12. The sensor mounting bracket attached to the wall and the sensor unit of claim 1, wherein the sensor unit includes a biological sensor that obtains biological information based on a reflection wave of a radio wave emitted therefrom.

* * * * *